United States Patent
Cairns et al.

(10) Patent No.: US 7,829,280 B2
(45) Date of Patent: Nov. 9, 2010

(54) PROCESS FOR REDUCING INTERFERENCES IN LUCIFERASE ENZYME ASSAYS

(75) Inventors: James E. Cairns, Toronto (CA); Phillip J. Whalen, Lower Kingsclear (CA); Patrick A. Whalen, Fredericton (CA)

(73) Assignee: LuminUltra Technologies Ltd., Fredericton, New Brunswick (CA)

( * ) Notice: Subject to any disclaimer, the term of this patent is extended or adjusted under 35 U.S.C. 154(b) by 457 days.

(21) Appl. No.: 11/626,907

(22) Filed: Jan. 25, 2007

(65) Prior Publication Data

US 2008/0182238 A1     Jul. 31, 2008

(51) Int. Cl.
*C12Q 1/68* (2006.01)
*G01N 33/53* (2006.01)

(52) U.S. Cl. ............................. 435/6; 435/7.1
(58) Field of Classification Search ............ 435/6, 435/7.1
See application file for complete search history.

(56) References Cited

U.S. PATENT DOCUMENTS 5,279,962 A *   1/1994   Gurtler et al. ............ 435/252.5
5,558,986 A     9/1996   Lundin
6,379,726 B1 *  4/2002   Tomasula .................... 426/89
7,556,933 B2 *  7/2009   Cairns et al. ................ 435/8
2003/0104507 A1 * 6/2003 Wood et al. .................. 435/8

OTHER PUBLICATIONS

Karl, D.M. and Larock, P.A., *Journal of the Fisheries Research Board of Canada* (1975), 32(5), 599-607.
Chen, B.R. and Smith, D.C., *Papers from the Summer Undergraduate Research Fellowship Program in Oceanography at The University of Rhode Island*, Graduate School of Oceanography and Department of Ocean Engineering, Narragansett, rhode Island, Jun.-Aug. 2003, http://espo.gso.uri.edu/~surfo/pubs/SURFO2003a.pdf.
Egeberg, K., *Proceedings of the Ocean Drilling Program, Scientific Results* (2000), 164, 393-398.
Nugent, C.E. et al., *Hydrobiologia* (1980), 70, 69-73.
Forsberg, C.W. and Lam, K., *Applied and Environmental Microbiology* (1977), 33(3), 528-537.
Cunningham, H.W. and Wetzel, R.G., *Limmonology and Oceanography* (1978), 23(1), 166-173.
Mollera, A. et al., *FEMS Microbiology Letters* (1995), 129(1), 43.
Spolaore, S. et al., *Journal of Experimental Botany* (2001), 52(357), 845-850.

* cited by examiner

*Primary Examiner*—Kenneth R. Horlick
(74) *Attorney, Agent, or Firm*—Harness, Dickey & Pierce, P.L.C.

(57) ABSTRACT

A method of conducting a biochemical assay that allows for a reduction of assay interferences. The method comprises treating a mixture of cell sample and cell constituents solubilizing agent, with an insoluble agent prior to conducting the assay. There is also provided a device as well as a kit for carrying out such assays.

17 Claims, 6 Drawing Sheets

12

PROCESS FOR REDUCING INTERFERENCES IN LUCIFERASE ENZYME ASSAYS

FIELD OF THE INVENTION

The invention relates generally to biochemical assays. In particular, the invention relates to a process for reducing assay interferences in biochemical assays. The invention also relates to apparatus as well as kits for carrying out such assays.

BACKGROUND OF THE INVENTION

Most problems encountered in biochemical assays including enzyme assays and assays involving nucleic acids, are due to interferences caused by substances such as heavy metals, surfactants, high salt concentrations and organic enzyme poisons. In the biochemical process of measuring biological cell constituents to identify cell species to estimate cell quantity, physiological status and activity, enzyme assays are especially powerful analytical tools because of their sensitivity and specificity. A specific example of enzyme assay in this application is the bioluminescent firefly luciferase assay that measures sample adenosine triphosphate (ATP), the main energy compound in living cells, within seconds with picogram sensitivity and minimal response produced by related compounds. The reaction catalyzed by the firefly luciferase enzyme is summarized by the following equation:

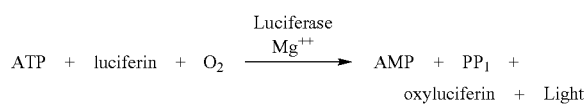

The routine use of enzyme in this assay can be compromised by factors such as the presence of sample contaminants that inhibit the enzyme reaction and/or create color and turbidity that interfere with the assay detection mechanism. In addition, the assay requires numerous pipetting steps and other sample processing procedures.

Various processes and techniques for reducing interferences in biochemical assays have been disclosed in the art. For example, chelating agents such as EDTA have been used in enzyme reagent mixtures to remove inhibition by heavy metals (Karl, D M and Larock, P A *Journal of the Fisheries research Board of Canada* (1975), 32(5), 5999-607). However, their benefit is limited because these agents themselves become inhibitory to the enzyme when their concentration is too high. Another option that has been routinely used in the art to prevent enzyme inhibition, color, and turbidity interference is to dilute the sample before or after processing for analysis. This approach has the disadvantage of reducing the sensitivity of the analysis. Furthermore, the requirement for large dilutions makes the analysis more cumbersome and/or increases the labor of the analysis. Also, when assay interferences are soluble, their removal by filtration has been employed by many users. However, filtration requires additional labor and material costs.

When measuring an analyte contained within biological cells such as ATP, it is also necessary to disrupt cell walls and membranes to permit the release of the analyte. Both mechanical processing and chemical releasing reagents are used to achieve this purpose. Physical methods such as boiling and high pressure techniques have been widely used in the art, but these methods are cumbersome because of the requirement of precise timing and/or an expensive, non-portable apparatus. Therefore, chemical agents such as acids, bases, organic solvents, and/or surfactants have been more frequently employed. However, such agents are themselves inhibitory to enzymes as their concentration increases. As a result, a compromise occurs between chemical agent strength and complete release of the analyte. With many commercial products currently available, the release of the analyte is incomplete. Stronger chemical agents in these situations are required for complete recovery of the analyte. However, use of stronger reagents requires dilution before enzyme assay with a consequential result of reduced assay sensitivity.

It is known in the art to minimize the extent of dilution by incorporating various agents in the assay reagents. For example, the buffer concentration used to maintain the reaction pH at optimal levels for enzyme activity is increased when acids or bases are used to permeabilize the cell wall. However, this approach still has limitations because the buffer itself becomes inhibitory as higher concentrations are used. To neutralize enzyme inhibition caused by releasing agents containing ionic surfactants, adding a surfactant with the opposite charge has been used. Cyclodextrin, a chemical with many molecular pores that can house hydrophobic molecules, has also been used successfully (U.S. Pat. No. 5,558,986 of Lundin). However, both these types of neutralizing agents, namely, surfactants and cyclodextrins are themselves inhibitory when their concentration is too high. Although cyclodextrins are less inhibitory than the surfactants, they are considerably more expensive.

In the processes known in the art and outlined above, the agents used to neutralize enzyme inhibitors are water soluble. Some teachings in the art have shown that insoluble particulate agents have potential advantages over soluble agents because the insoluble agents can easily be separated from the treated cell solution by rapid settling or screening and therefore do not interact with the enzyme. Examples of insoluble agents include anion and cation exchange resins, chelating resins, and absorbent resins.

A number of researchers have successfully used strong acid cation exchange resins to remove metal inhibition following ATP extraction from microorganisms by sulfuric or phosphoric acid (Chen, B R and Smith, D C, *Papers from the Summer Undergraduate Research Fellowship Program in Oceanography at The University of Rhode Island*, Graduate School of Oceanography and Department of Ocean Engineering, Narrragansett, R.I., June-August, http://espo.gso.uri.edu/~surfo/pubs/SURF02003a.pdf; Egebert, K, *Proceedings of the Ocean Drilling Program, Scientific Results* (2000), 164, 393-398; Nugent, C E et al., *Hydrobiologia* (1980), 70, 69-73); Forsberg, C W and Lam, K, *Applied and Environmental Microbiology* (1977), 33(3), 528-537; and Cunningham, H W and Wetzel R G, *Limmonology and Oceanography* (1978), 23(1), 166-173). Some of these researchers compared this approach with the approach involving the use of the chelating agent EDTA to neutralize metal inhibition. They found that the approach using a resin is more efficient (Cunnigham and Wetzel).

Polyvinylpolypyrrolidone (PVPP) is another insoluble agent that has been used to remove inhibitors in enzyme assays such as the ATP assay (Mollera, A et al., *FEMS Microbiology Letters* (1995), 129(1), 43; and Spolaore, S et al., *Journal of Experimental Botany* (2001), 52(357), 845-850). In most of these references, the use of the insoluble agent involves the neutralization of phenolic components in plant extracts.

There is therefore a need for more efficient and cost effective processes for reducing interferences in biochemical assays.

SUMMARY OF THE INVENTION

The inventors have now discovered that by treating a sample with an insoluble agent prior to conducting the assay, the interferences are greatly reduced, thus leading to more accurate results for the assay. In particular in enzyme assays, the insoluble agents are easily separated from the sample and therefore do not interact with the enzyme.

The inventors have also discovered an apparatus that can be used to carry out the process according to the invention. The apparatus is simple, portable and economic and allows for automation.

The invention thus provides according to a first aspect, for a method of conducting a biochemical assay on a cell sample. The method comprises the steps of: (a) mixing the cell sample with a cell constituents solubilizing agent to obtain a first mixture; (b) treating the first mixture with an insoluble agent to obtain a second mixture; and (c) treating the second mixture with a biochemical assay reagent or system reagent.

The method according to the invention can be used in connection with biochemical assays such as enzyme assays, assays involving nucleic acids, or immunoassays. The biochemical assay can also be firefly luciferase enzyme assay, DNA or RNA amplification, or DNA or RNA cleavage. In a preferred embodiment, the biochemical assay can be firefly luciferase enzyme assay.

The insoluble agent used in the method according to the invention can be a chelating resin, an ion exchange resin, an absorbent resin, polyvinylpolypyrrolidone, or a mixture thereof. In a preferred embodiment, the insoluble agent can be a chelating resin. Optionally, the chelating resin may have an iminodiacetic acid group. The insoluble agent can be used in combination with a soluble agent or a fluid that can be selected from the group consisting of diluents, neutralizers of enzyme inhibitors, chelating agents, cyclodextrins, branched dextrins, and mixtures thereof. In preferred embodiments, the chelating agents used in combination with the insoluble agent may be selected from the group consisting of ethylenediamine, ethylenediaminetetraacetic acid (EDTA), ethylene glycol tetraacetic acid (EGTA), porphyrins, and mixtures thereof. The insoluble agent can be in a form including but not limited to powder, pelletized powder, bead, membrane, mesh, and mixtures thereof.

The cell constituents solubilizing agent used in the method according to the invention may comprise a surfactant, a high pH phosphate buffer, a base, or mixtures thereof. The high pH phosphate buffer may comprise a tribasic monovalent phosphate salt which can be trisodium phosphate, tripotassium phosphate, trilithium phosphate or mixtures thereof. In a preferred embodiment, the tribasic monovalent phosphate salt can be at a concentration of about 0.5 to 500 mM. Optionally, the tribasic monovalent phosphate salt can be at a concentration of about 5 mM. The surfactant may be selected from a cationic surfactant and a non-ionic surfactant. When the surfactant is a cationic surfactant, it can be a quaternary ammonium salt or a phosphonium salt. When the surfactant is a non-ionic surfactant, it can be an octylphenol ethoxylate. In a preferred embodiment, the surfactant can be benzalkonium chloride or tributyl (tetradecyl) phosphonium chloride. The surfactant can be at a concentration of about 100 to 10,000 mg/L. Optionally, the surfactant can be at a concentration of about 1000 to 4000 mg/L.

According to a second aspect, the invention provides for a device for conducting a biochemical assay on a cell sample. The device comprises: a plurality of interconnectable compartments, one of the compartments suitable for containing a cell constituents solubilizing agent, and at least one of the remaining compartments suitable for containing an insoluble agent; top and bottom compartments each having a closure means adapted to allow access to the interior of the compartment; and interconnection means for interconnecting the compartments, at least one of the interconnection means comprising a mechanical control means actionable by a user and adapted to allow for a fluid communication between selected compartments.

The invention provides according to a third aspect, for a device for conducting a biochemical assay on a cell sample. The device comprises: a plurality of interconnected compartments, one of the compartments containing a cell constituents solubilizing agent, and at least one of the remaining compartments containing an insoluble agent; top and bottom compartments each having a closure means adapted to allow access to the interior of the compartment; and interconnection means interconnecting the compartments, at least one of the interconnection means comprising a mechanical control means actionable by a user and adapted to allow for a fluid communication between selected compartments.

In the above second and third aspects of the invention, the device can be used to carry out the method according to the invention. Thus the device can be used to carry out biochemical assays such as enzyme assays, assays involving nucleic acids, or immunoassays. The biochemical assay can also be firefly luciferase enzyme assay, DNA or RNA amplification, DNA or RNA cleavage, or DNA or RNA insertion. In a preferred embodiment, the biochemical assay can be firefly luciferase enzyme assay. The biochemical assays in the second and third aspects of the invention, can be conducted in accordance with the method of the invention as described above.

The mechanical control means associated to the device according to the invention may be a valve, a penetrable septum, a breakable seal, or any other suitable mechanical control means that requires to be operated by a user.

In a preferred embodiment, at least one of the remaining compartments suitable for containing or containing the insoluble agent may comprise at least one filtration means located adjacent the interconnection means or the closure means. Optionally, the filtration means can be made of same material as the insoluble agent. The interconnection means may also comprise a filtration means that can be made of same material as the insoluble agent.

In a preferred embodiment, at least one of the top and bottom closure means may comprise a liquid dispensing means. Optionally, the liquid dispenser means may comprise a filtration means that can be made of same material as the insoluble agent. Furthermore, at least one of the top and bottom closure means may comprise a liquid dispensing means which can be selected from the group consisting of droppers, dipsticks, ladles, pumps, ampoules, squeezable chamber, loops, syringes, pipettes, and combinations thereof. Optionally, the liquid dispensing means can be adapted to receive an assay vessel. In addition, the assay vessel may contain a biochemical assay reagent or system reagent.

In a preferred embodiment, the interior of at least one of the compartments can be made of same material as the insoluble agent. Also, at least one of the interconnected compartments can be a volumetric chamber. Optionally, the volumetric chamber can be directly connected to the top or bottom compartment. At least one of the compartments not containing the cell constituents solubilizing agent or the insoluble agent may contain a diluent. Furthermore, the top closure means may comprise a transfer pipette and the bottom closure means may comprise a dropper.

According a fourth aspect, the invention provides for a kit for conducting a biochemical assay on a cell sample. The kit comprises separate components of the device according to the invention. Optionally, the kit may comprise instructions for constructing the device.

According to a fifth aspect, the invention provides for a kit for conducting a biochemical assay on a cell sample. The kit comprises: separate components of the device according to the invention; a first container containing a cell constituents releasing agent; a second container containing an insoluble agent; and one or more assay vessels containing a biochemical assay reagent or reagent system. Optionally, the kit may comprise instructions for constructing the device and/or instructions for conducting the assay.

According to a sixth aspect, the invention provides for a kit for conducting a biochemical assay on a cell sample. The kit comprises: the device according to the invention; and one or more assay vessels containing a biochemical assay reagent or reagent system. Optionally, the kit may comprise instructions for conducting the assay.

In the above fourth, fifth and sixth aspects of the invention, the kit can be used to perform the method according to the invention. Thus the kit can be used to carry out biochemical assays such as enzyme assays, assays involving nucleic acids or immunoassays. The biochemical assay can also be firefly luciferase enzyme assay, DNA or RNA amplification, or DNA or RNA cleavage. In a preferred embodiment, the biochemical assay can be firefly luciferase enzyme assay. The biochemical assays in the fourth, fifth and sixth aspects can be conducted in accordance with the method of the invention as described above.

BRIEF DESCRIPTION OF THE DRAWINGS

These and other advantages of the invention will become apparent upon reading the following detailed description and upon referring to the drawings in which.

Figure 1:
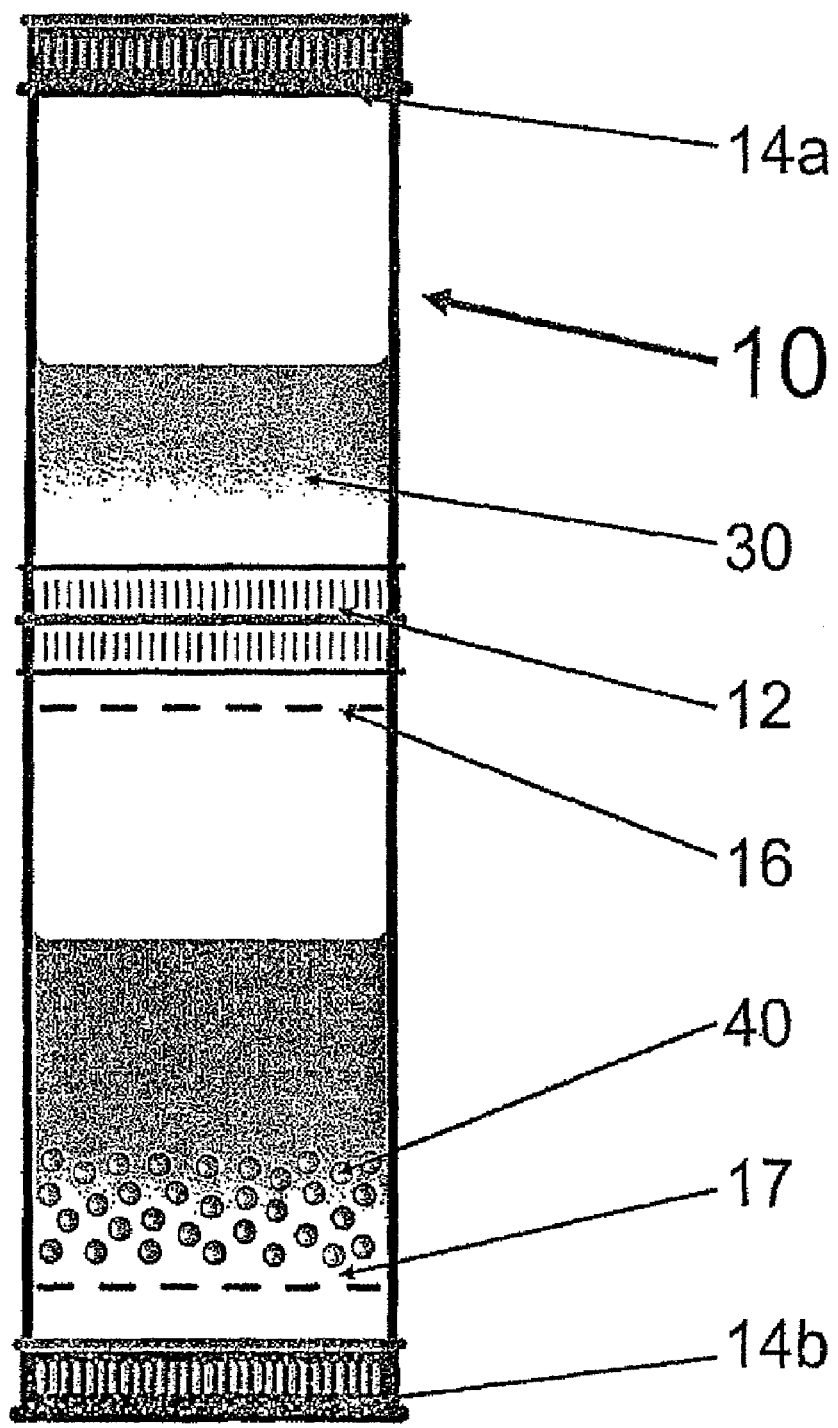
FIG. 1 illustrates a device according to the invention.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE PREFERRED EMBODIMENTS

With the exception of strong acid cation exchange resins and PVPP, insoluble agents have not been used to neutralize compounds that interfere with the luciferase assay. Although the conventional use of chelating resins is to remove metals from solution, the inventors have discovered that chelating resins with an iminodiacetic acid functional group can also remove cationic surfactants from ATP solutions. This is illustrated by the following experiment.

Example 1

A trisodium phosphate buffer solution containing 10 nanograms ATP per mL and 1000 mg/L of alkyl dimethybenzyl ammonium chloride (ADBAC) was assayed for ATP by mixing 100 microliters of this solution with 100 microliters of luciferase reagent. The light produced in this reaction was measured in a luminometer (Kikkoman C-100 Lumitester). Several dilutions of this ATP solution were also prepared in phosphate buffer and tested. In addition, a 3 mL portion of this solution was mixed with 1 mL of a chelating resin (IRC748, Rohm and Haas Company) and similarly diluted in phosphate buffer, then assayed for ATP.

The results are summarized in Table 1. When an ATP solution free of enzyme inhibitors is diluted in half, the light produced in the reaction is one half of the full strength solution. If an inhibitor is present, the light produced is a one-strength solution is more than half of the full strength solution because the reaction is less inhibited. As shown in Table 1, phosphate buffer ATP solution containing 1000 mg/L ADBAC must be diluted by a factor of 8 to overcome luciferase inhibition. However, when the solution was pretreated with the chelating resin, the solution only had to be diluted by a factor 4. Also noteworthy is that the resin pretreatment, while not completely overcoming the inhibition of the full strength dilution, increased the response of the reaction by more than a factor of 10. This increase in detection capability is extremely significant because for applications in which ATP is used to detect emerging growth of microbial contaminants, the increased sensitivity provides an earlier warning. Because antimicrobial treatment is more effective at lower levels of contamination, this provides an advantage. Increased ATP assay sensitivity can alternatively be achieved by increasing the concentration of the luciferase reagent, but because the luciferase reagent is very expensive, increasing the assay sensitivity by other means is more cost-effective.

TABLE 1

Reduction of ADBAC Inhibition of Luciferase by Chelating Resin IRC-748. RLU is an abbreviation for Relative Light Units (the display on the Luminometer after the light of the bioluminescent reaction has been measured over a 10 second interval).

| Dilution | No resin treatment RLU | Pre-treatment with IRC-748 RLU |
| --- | --- | --- |
| none | 1,254 | 13,231 |
| 1/2 | 1,549 | 34,992 |
| 1/4 | 16,362 | 24,876 |
| 1/8 | 11,725 | 11,957 |
| 1/16 | 6,036 | 6,100 |

Table 1 outlines the results obtained from an experiment of assaying a 10 ng/mL ATP standard solution in phosphate buffer containing 1000 mg/L alkyl dimethybenzyl ammonium chloride (ADBAC), following dilution in a phosphate buffer, with and without pre-treatment with the chelating resin IRC-748.

Example 2

In this experiment, a phosphate buffer also containing 1000 mg/L ADBAC is used to extract ATP from a sample containing microorganisms. 2 mL of a sample from the effluent of a municipal sewage plant was mixed with 2 mL of the ADBAC solution. The ATP released by this process was measured in a Kikkoman luminometer by mixing 100 microliters of the mixture and combining it with 100 microliters of a luciferase assay mixture. Several dilutions of this ATP extract were also prepared in phosphate buffer and tested. In addition, a 3 mL portion of the ATP extract was mixed with 1 mL of a chelating resin (IRC748, Rohm and Haas Company) and similarly diluted in phosphate buffer, then assayed for ATP. The results of this experiments and presented in Table 2.

The advantage provided by the resin treatment of the sample ATP extract is similar in this instance. Furthermore, the detection limit of the assay is 15 times higher when an undiluted extract is measured (This result is shown in the row in which the ADBAC is diluted by ½. This degree of ADBAC dilution occurs when the ADBAC ATP releasing agent is mixed with sample.)

TABLE 2

Firefly Luciferase Assay for ATP in a Sample of Wastewater Effluent

| Dilution of ADBAC in ATP Extract | No Extract treatment (RLU) | Extract treated With chelating resin (RLU) |
|---|---|---|
| ½ | 1,489 | 21,860 |
| ¼ | 4,658 | 18,051 |
| ⅛ | 6,512 | 8,842 |
| 1/16 | 4,628 | 4,297 |
| 1/32 | 2,401 | 2,304 |

The ATP extract in this experiment was produced by mixing a solution containing 1000 mg/L ADBAC in phosphate buffer. Further dilutions were made in a phosphate buffer. The chelating resin was IRC-748. The resin treatment consisted of mixing 1 mL of resin with 3 mL of extract, then allowing the resin beads to settle before ATP analysis.

Example 3

The results obtained in another experiment conducted on the same source of wastewater sampled on a different date, show that the ADBAC inhibition can be completely overcome by treating the extract with 2 portions of resin. Doubling the volume of resin in a single treatment was almost as effective. The results are summarized in Table 3.

TABLE 3

Luciferase Assay for ATP in a Sample of Wastewater Effluent

| Dilution of ADBAC in ATP Extract | No extract pre-treatment RLU | Extract treated with 2 mL chelating resin RLU | Extract treated with two 1 mL portions of chelating resin RLU |
|---|---|---|---|
| ½ | 209 | 13,282 | 16,031 |
| ¼ | 7,310 | 8,055 | 8,132 |
| ⅛ | 6064 | 4,149 | 4,119 |
| 1/16 | 3100 | 2,099 | 2,134 |
| 1/32 | 1551 | 1,103 | 1,107 |

The ATP extract in this experiment was produced by mixing a solution containing 1000 mg/L ADBAC in phosphate buffer. Further dilutions were made in a phosphate buffer. The chelating resin was IRC-748. The resin treatment consisted of mixing 2 mL of resin with 3 mL of extract, then allowing the resin beads to settle before ATP analysis. In a variation of this analysis, 3 mL of sample were treated with 1 mL of resin and the supernatant of this treatment was treated to a second 1 mL portion of resin prior to ATP analysis.

Example 4

In a further experiment, we also have found that ion exchange resins are less effective than chelating resins in reducing ADBAC inhibition of luciferase using assay conditions according to the invention. This is demonstrated by experimental results summarized in Table 4. The experiment was conducted in the same format as described for the first experiment by testing an ATP standard solution spiked with ADBAC. The dilution required to remove inhibition following treatment with an ion-exchange resin was the same as the test condition in which no resin treatment was applied. In contrast, a ¼ fold dilution removed almost all of the inhibition in the solution that had been pre-treated with the chelating resin. Again, the luciferase activity in an undiluted solution treated with the chelating resin provided a response many times greater than untreated solution or solution treated with ion exchange resins.

TABLE 4

Inhibition of Luciferase Activity After Treatment with Various Resins

| | Luciferase Activity (% of activity in the absence of ADBAC) | | | | |
|---|---|---|---|---|---|
| dilution | none | IRC-748 Chelating resin | IR-120 Na Strong acid cation exchange | IR-120 H Strong acid cation exchange | IRA-67 Weak base anion exchange |
| None | 0.01% | 15% | 0.60% | <0.01% | 5% |
| ½ | 6.7% | 57% | 9.2% | 2.2% | 20% |
| ¼ | 33% | 95% | 62% | 50% | 71% |
| ⅛ | 100% | 100% | 100% | 100% | 100% |
| 1/16 | 100% | 100% | 100% | 100% | 100% |

Table 4 outlines the results obtained from an experiment of assaying a 10 ng/mL ATP standard solution in phosphate buffer containing 1000 mg/L alkyl dimethybenzyl ammonium chloride (ADBAC), following dilution in a phosphate buffer, with and without various resin pretreatments. It should be noted that Table 4 is constructed from results of 2 different experiments. In order to facilitate comparison, the results are expressed as enzyme activity instead of instrument reading. Luciferase activity was calculated by dividing the RLU of each test condition by the RLU of an uninhibited reaction and expressing the results as a percentage.

Example 5

Other experiments determined that insoluble agents could be used in combination with soluble agents to cause further reductions in enzyme inhibition. Results obtained from an example experiment are outlined in Table 5. An initial solution containing 7200 mg/L ADBAC and 1 ng ATP per mL was prepared in phosphate buffer. A stronger concentration of ADBAC was used in this experiment to facilitate the observation of the degree of neutralization. Four dilution series were prepared from this stock solution. One series was diluted only in a phosphate buffer. Another identical series was prepared in the phosphate buffer but was pre-treated with IRC-748 chelating resin (3 parts solution treated with one part resin) prior to assaying for ATP. The third dilution series was made in a phosphate buffer containing p-cyclodextrin (a soluble compound that can neutralize ADBAC) so that each member of the series contained 3,750 β-cyclodextrin. The fourth series was prepared in the same way as the third series, except that each member of the series was pre-treated with IRC-748 chelating resin (3 parts solution treated with one part resin) prior to assaying for ATP. All solutions were assayed for ATP by mixing 100 microliters of solution with 100 microliters of luciferase reagent and measuring the light produced in a Kikkoman luminometer.

An examination of the results outlined in Table 5 shows that luciferase activity is low in the set with the highest amount of ADBAC (2 fold dilution), except in the assay of the solution treated with both resin and cyclodextrin. With further dilution the combination treatment shows no advantage over the resin pre-treatment only. However, with neither resin nor cyclodextrin treatment at least a 16 fold dilution is required to prevent suppression of enzyme activity.

While this example shows an advantage of using the combination of soluble and insoluble agents only at a very strong ADBAC concentration, it is a very simple chemical system. In the complex environment found in industrial and domestic waters, the benefits could be greater because the range of types of chemicals neutralized by combinations of different agents is likely to be extended.

TABLE 5

Combined Treatment of Soluble and Insoluble Neutralizers of Enzyme Inhibitors

| | Treatment | | |
|---|---|---|---|
| Dilution | β-cyclodextrin | Resin pre-treatment | RLU |
| 1/2 | N | N | 5 |
| 1/2 | Y | N | 3 |
| 1/2 | N | Y | 156 |
| 1/2 | Y | Y | 1204 |
| 1/4 | N | N | 6 |
| 1/4 | Y | N | 96 |
| 1/4 | N | Y | 1796 |
| 1/4 | Y | Y | 1804 |
| 1/8 | N | N | 58 |
| 1/8 | Y | N | 1227 |
| 1/8 | N | Y | 1065 |
| 1/8 | Y | Y | 1029 |
| 1/16 | N | N | 423 |
| 1/16 | Y | N | 606 |
| 1/16 | N | Y | 563 |
| 1/16 | Y | Y | 519 |

The experiment described in Example 5 compares the ability of a soluble agent (β-cyclodextrin) and an insoluble agent (chelating resin, IRC-748) and their combination to neutralize the inhibition of the bioluminescent reaction catalyzed by firefly luciferase.

In the first members of the dilutions series, the ATP solution contained 0.5 ng ATP per mL and 3600 mg/L ADBAC. A concentrate of cyclodextrin was added to the ATP solutions in some of the tests to maintain concentration of 3,750 mg/L through the dilution series.

It can be seen from the Examples described above that the use of insoluble agents improves the sensitivity and accuracy of tests for biological cell components such as the firefly luciferase assay for ATP. The inventors have further discovered that this process can be incorporated into devices, thus allowing for a reduction of skill and labor requirements generally associated with such tests.

The process according to the invention can be conducted in the device designed by the inventor. The device is simple and easy to operate and allows for a significant reduction of labor and therefore cost savings. The device also allows for automation.

DESCRIPTION OF A PREFERRED EMBODIMENT OF THE DEVICE

Referring to FIG. 1, an embodiment of the device according to the invention and generally represented by reference numeral 10, consists of two interconnecting compartments in which the first compartment contains a cell constituents solubilizing or releasing agent 30 and the second compartment contains an insoluble agent 40 that removes assay interferences. The connection 12 between the two compartments contains a valve to control the flow of liquid between the compartments, while the other ends of the compartments are sealed with removable or penetrable lids 14a and 14b.

The insoluble agent 40 could consist of a single component or a mixture of components. The insoluble agent 40 could be dry, moist, or mixed with a fluid. The fluid could be simply a diluent or could contain other reagents, including soluble neutralizers of enzyme inhibitors such as EDTA and/or a cyclodextrin. The insoluble agent could be in a variety of forms including a powder, pelletized powder, bead, membrane, or a mesh. The insoluble agent could consist of a mixture of these forms. Furthermore, the insoluble agent could consist of insoluble components pre-treated with liquid reagents. In FIG. 1, the insoluble agent 40 is a resin combined with a fluid. The chamber containing the insoluble agent 40 includes an optional mesh 16 placed after the valve of the first chamber. The mesh itself could be made of a material that removes enzyme inhibitors as could the walls of the chamber containing the insoluble agent. The mesh structure may also be built into the connection 12.

An alternative to the removable lids 14a and 14b, in particular to the removable lid 14a, could be a valve device that allows access to the top chamber. In either case, the lid is adapted to permit introduction of a sample. After introduction of the sample, the lid or valve 14a is closed and the device is shaken or inverted in order to mix the sample with the cell constituents solubilizing agent 30 in the top chamber. After sufficient time has elapsed for the sample to react with the reagent, the valve 12 to the second chamber is opened so that the mixture can be exposed to the insoluble agent 40 that neutralizes assay interferences either from the sample and/or from the cell solubilizing or releasing agent 30. The connection 12 may be closed or left opened after the transfer. By shaking or inverting the device several times, neutralization of enzyme inhibitors is achieved. The product of these reactions can be sampled and analyzed by sampling the contents of the entire mixture, either from the top or bottom of the cartridge. However, if further optional mesh 17 placed at the bottom of the chamber containing the insoluble agent is included in the device, the preferred sampling location would be the bottom of the cartridge. The mesh structure 17 provides a further advantage of reducing assay interferences caused by turbidity and also retaining the insoluble neutralization agent 40.

Many useful variations of this basic unit are conceivable and will be apparent to skilled persons, but the invention would not be limited to these variations. Examples of such variations are shown in FIGS. 2 to 6.

Figure 2:
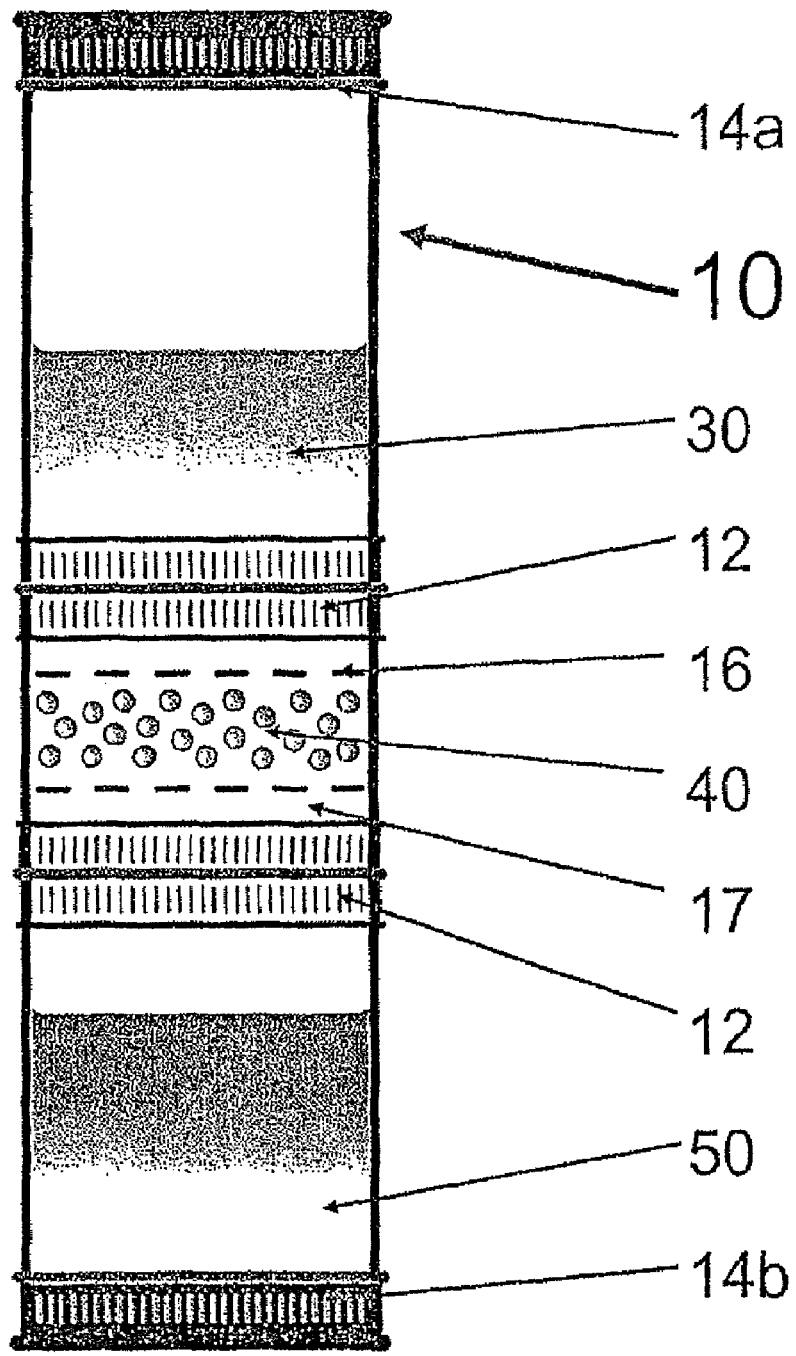
FIG. 2 illustrates an embodiment of the device according to the invention.

FIG. 2 illustrates an embodiment in which an additional chamber is added to the device. The additional chamber might include additional insoluble agent 40 or insoluble agent in combination with soluble agent, as well as mesh structures. In FIG. 2, a second optional mesh 17 in the middle chamber retains the insoluble agent 40 and allows for filtration of particulates of the sample. The mesh structures 16 and 17 may be built into the connection 12. The design shown in FIG. 2 also permits isolation of the insoluble agent 40 in the middle chamber. The bottom chamber contains a diluent and/or reagent 50. However, another variation of this embodiment could have the insoluble agent 40 placed in the bottom chamber, while the diluent and/or reagent 50 is placed in the middle chamber. It should be noted that even more chambers could be added to the device providing for further variations.

Figure 3:
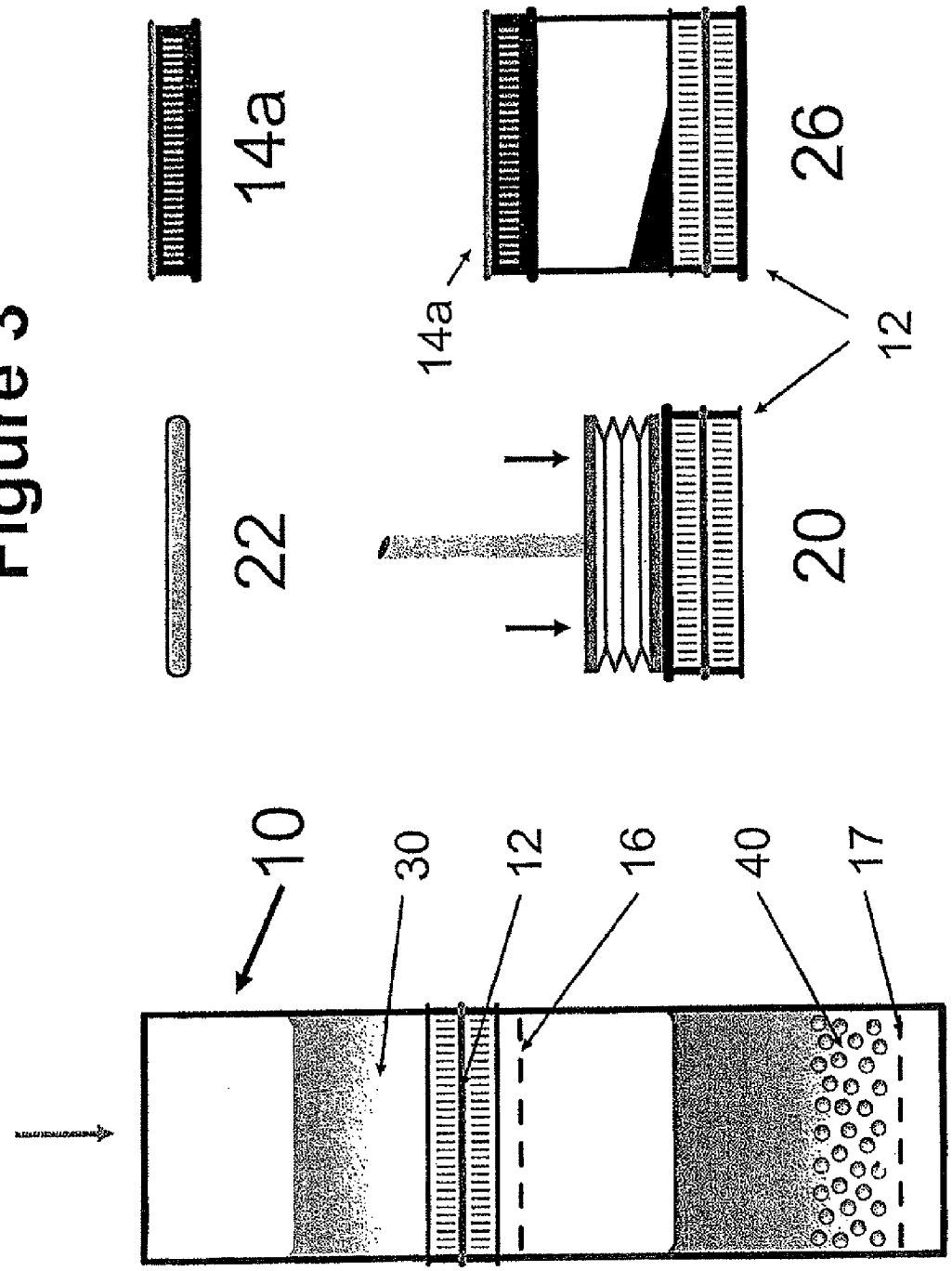
FIG. 3 illustrates embodiments of the top compartment of the device according to the invention.
Figure 4:
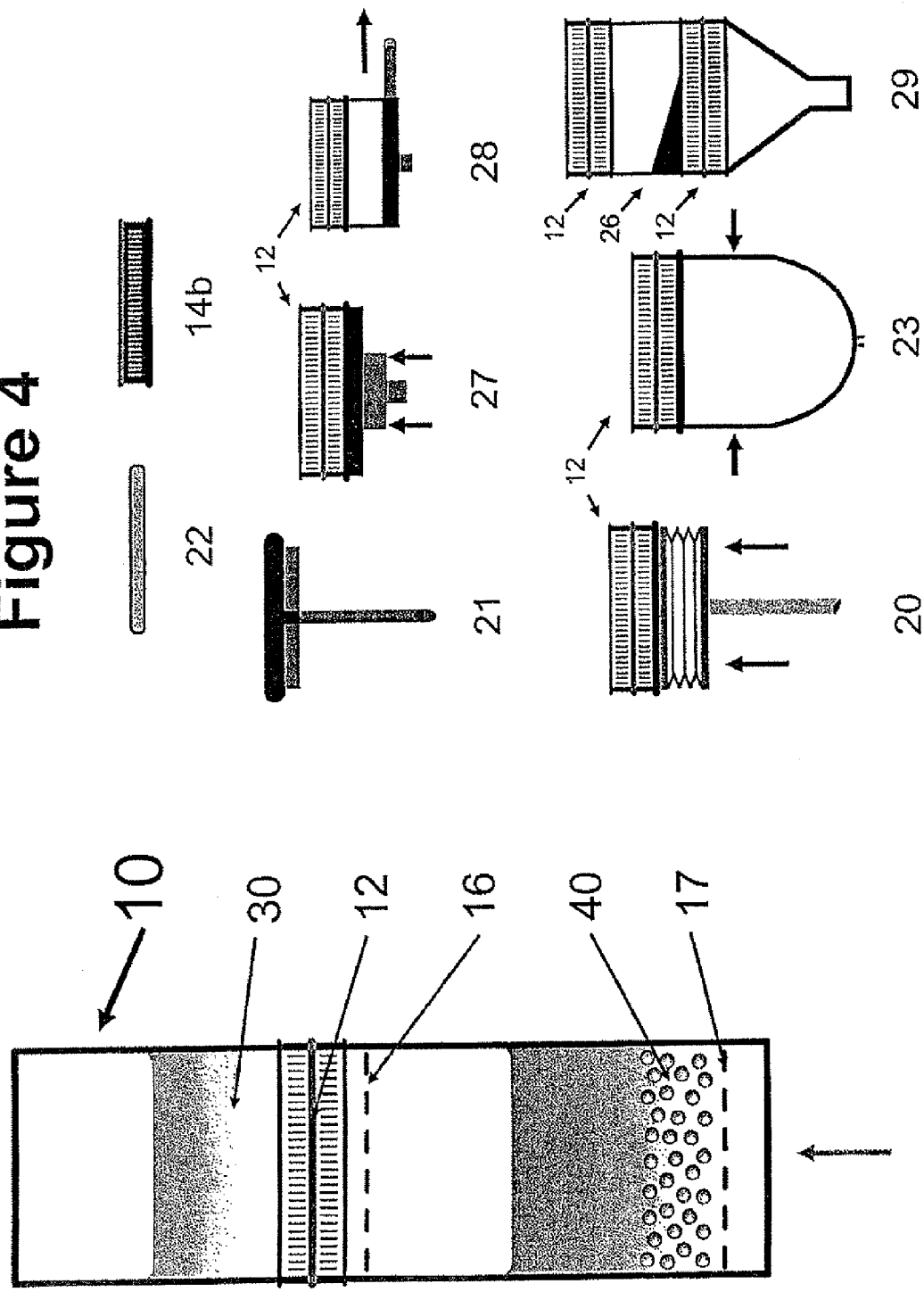
FIG. 4 illustrates embodiments of the bottom compartment of the device according to the invention.

Other embodiments of the device according to the invention are illustrated in FIGS. 3 and 4. In these variations, liquid dispensing devices such as droppers, dipsticks, ladles, pumps, ampoules, loops, syringes, or pipettes can be integrated to the device, preferably at one or both of the caps.

Some examples of options for the top closure cap for the cartridge are illustrated in FIG. 3. These options include lids such as a penetrable seal 22 or a removable cap 14a. Further options for the top closure cap also include mechanical options such as a bellowed pipette 20 and a volumetric chamber 26. The bellowed pipette 20 or the volumetric chamber 26 may or may not include a connection 12. The bellowed pipette 20 is utilized by compressing the bellows to retrieve the liquid sample. The volumetric chamber is a calibrated chamber of a specific volume that can be used by simply pouring in the sample for accurate transfer.

Some examples of options for the bottom closure cap for the cartridge are illustrated in FIG. 4. These options include lids such as a penetrable seal 22 and a removable cap 14b. A dipstick 21 or a bellowed pipette 20 described above. A push-action dispenser 27 can be used to accurately dispense a volume of prepared sample into an assay vessel (not shown). A volumetric chamber 26 complete with a knife-gate valve 28 can be used to dispense an accurate amount of prepared sample into an assay vessel. A squeeze-bulb dispenser 23 can be used to dispense prepared sample into an assay vessel. A nozzle 29 can be used to transfer into the assay process by using a series of connections 12 and a volumetric chamber 26. It should be noted that the bellowed pipette 20, the push-action dispenser 23, the volumetric chamber 26, the squeeze-bulb dispenser 23 as well as the nozzle 29, may or may not include a connection 12.

Figure 5:
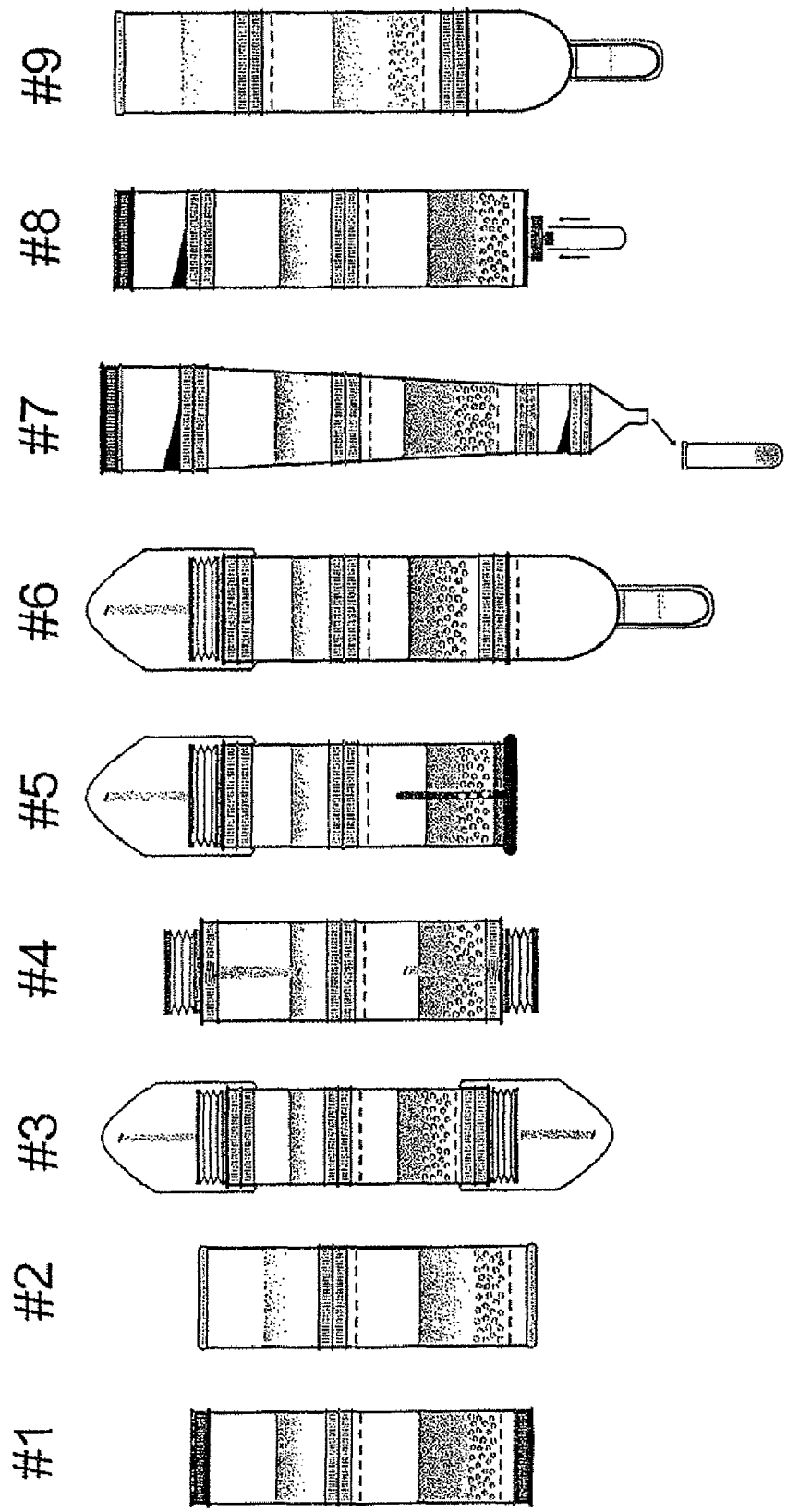
FIG. 5 illustrates further embodiments of the top and bottom compartments of the device according to the invention.

FIG. 5 provides various arrangements of the overall cartridge device according to the invention. In particular, FIG. 5 presents different arrangements including variations of liquid dispensing devices that can be used in combination with the device according to the invention. These combinations are meant to present possible examples of top and bottom chamber closures and are not meant to be exhaustive.

Arrangement #1 illustrates the basic device according to the invention, in which top and bottom closures are removable lids.

Arrangement #2 illustrates an example where the top and bottom closures are penetrable seals. This variation of the device would present a suitable arrangement to facilitate automated and/or on-line usage of the device.

Arrangement #3 illustrates an example in which transfer pipettes are integrated into the device via a shrink wrap or cap.

Arrangement #4 illustrates an example in which the pipettes also participate in the top and bottom closure of the device's chambers.

In arrangement #5, a transfer pipette is integrated into the top chamber via a shrink wrap or cap and a dipstick participates in the closure of the bottom chamber.

Arrangement #6 illustrates an example in which the device contains all components necessary for an ATP assay. The top of the device contains a pipette to collect and deliver the sample containing microorganisms to the first chamber. When the sample is mixed with the ATP releasing agent in the upper chamber, ATP is released from within microorganisms into the surrounding liquid. When the valve below the ATP releasing agent is opened and the contents of the upper chamber are mixed with the contents of the chamber below it, the resin neutralizes a portion of the enzyme inhibitors. The diluent reduces the concentration of the remaining inhibitors to a non-inhibitory level. A portion of this mixture is ready to be delivered to the luciferase reagent. This is achieved by opening the bottom valve to a squeezable chamber that functions as a dropper bottle. A final clarification of ATP solution is achieved by a mesh in the dropper bottle component. By delivering a drop of the ATP solution to the luciferase, the bioluminescent reaction is initiated and the light produced in the reaction is measured in a luminometer.

Arrangement #7 illustrates an example in which the volume of additional chambers installed on the device are used as a means to precisely measure and transfer solution volumes without the use of calibrated volume transfer equipment. The user removes the cap from the top of the device and fills the chamber up with a well-mixed sample. This new chamber is constructed to hold an exact volume of fluid. A valve connects the opening of this chamber to the second chamber, and another valve further connects to a third chamber containing the insoluble agent. A third valve then connects to the fourth chamber, which again has a precise volume to contain sufficient prepared sample for the analyte assay process. A fourth valve is used to release this volume through a nozzle and into an assay vessel.

Arrangement #8 is similar to #7 described above except that the bottom volumetric chamber is replaced by a push-action dispenser.

Arrangement #9 is similar to #6 except that the top chamber is a penetrable lid and the bottom chamber contains the same dispensing mechanism as in arrangement #6. Such arrangement would be suitable for a low-cost, self-contained automated format.

Figure 6:
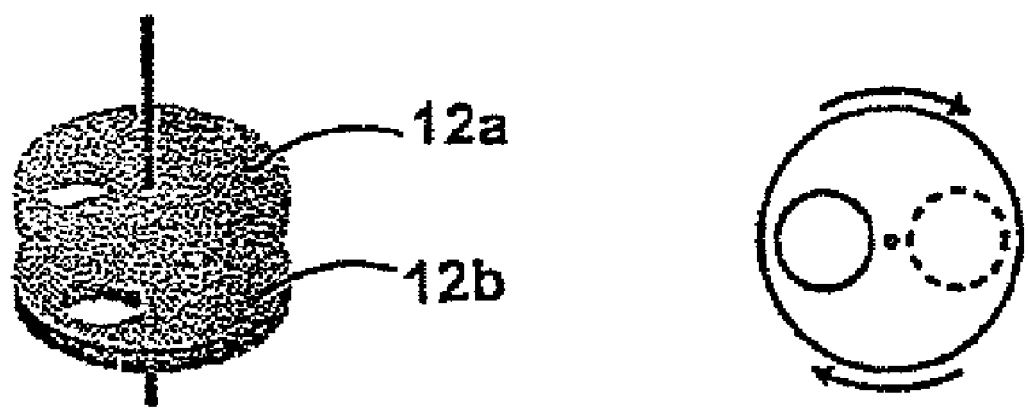
FIG. 6 illustrates an embodiment of the interconnected means of the device according to the invention.

FIG. 6 illustrates an embodiment of a valve associated with connection 12, that can be used in the device according to the invention. As illustrated, the valve can be a twist valve. It should be noted that the valve can also be a penetrable septum, a breakable seal, or any other mechanism suitable for separating two connected chambers and that requires a physical intervention by a user to achieve fluid communication between the chambers. Such valve system is well known in the art and will be apparent to skilled persons. A mesh structure can be installed into one or both of the openings of the pair of discs 12a and 12b.

It can be seen that the inventors have designed a process and apparatus that allow for alleviation of at least some problems caused by interfering substances in biochemical assays. The process presents numerous advantages and benefits. For example, the detection limit of the assay can be increased without using concentration techniques such as filtration; this reduces labor and equipment costs and can increase the variety of applications for the assay. The invention also provides for the potential to lower reagent costs by limiting the amount of expensive components such as assay enzymes required for successful measurement. In addition and particularly for enzyme assays such as ATP assays, the invention allows for the use of stronger cell permeabilizers and cell component releasing agents, thus improving the accuracy of the analysis and minimizing the time required for the solubilization of cell components. Moreover, the invention provides for the removal of the need for filtration for many types of samples, thus reducing costs and labor, and elevating portability. The invention further provides for the possibility to simplify biochemical analyses and to introduce low-cost and low-maintenance automation and/or on-line analysis formats.

While the foregoing description has described preferred modes currently contemplated for practicing the invention, the scope of the invention is not intended to be limited by this description and these examples. Various alternative combinations of the process and device according to the invention are contemplated as being within the scope of the following claims particularly pointing out and distinctly claiming the present invention.

What is claimed is:

1. A method of performing an assay for ATP on a sample comprising a solution containing cells having intracellular ATP, comprising the steps of:
    (a) disrupting the walls of said cells by contacting said cells with a cationic surfactant and an alkaline phosphate salt, to release said ATP from the interior of said cells into said solution;
    (b) removing the cationic surfactant from said solution by contacting said solution with an insoluble chelating agent; and
    (c) assaying said solution for ATP.

2. A method as defined in claim 1, wherein the insoluble chelating agent includes an iminodiacetic acid group.

3. A method as defined in claim 1, wherein the insoluble chelating agent is used in combination with a soluble agent or a fluid.

4. A method as defined in claim 1, wherein the insoluble chelating agent is used in combination with a component selected from a diluent, a neutralizer of enzyme inhibitors, a soluble chelating agent, a cyclodextrin, a branched dextrin, a base in addition to said alkaline phosphate salt and mixtures thereof.

5. A method as defined in claim 4, wherein the soluble chelating agent is selected from ethylenediamine, ethylenediaminetetraacetic acid (EDTA), ethylene glycol tetraacetic acid (EGTA), porphyrins, and mixtures thereof.

6. A method as defined in claim 1, wherein the insoluble chelating agent is in a form selected from powder, pelletized powder, bead, membrane, mesh, and mixtures thereof.

7. A method as defined in claim 1, wherein the alkaline phosphate salt comprises a tribasic monovalent phosphate salt selected from trisodium phosphate, tripotassium phosphate, trilithium phosphate and mixtures thereof, optionally the tribasic monovalent phosphate salt is at a concentration of about 0.5 to 500 mM, optionally the tribasic monovalent phosphate salt is at a concentration of about 5 mM.

8. A method as defined in claim 1, wherein the cationic surfactant is selected from a quaternary ammonium salt and a phosphonium salt.

9. A method as defined in claim 1, wherein the cationic surfactant is benzalkonium chloride or tributyl (tetradecyl) phosphonium chloride.

10. A method as defined in claim 1, wherein the cationic surfactant is at a concentration of about 100 to 10,000 mg/L, optionally the surfactant is at a concentration of about 1000 to 4000 mg/L.

11. A method of performing an assay for ATP on a sample comprising a solution containing cells having intracellular ATP, comprising the steps of:
    (a) disrupting the walls of said cells by contacting said cells with a cationic surfactant, to release said ATP from the interior of said cells into said solution;
    (b) removing the cationic surfactant from said solution by contacting said solution with an insoluble chelating agent; and
    (c) assaying said solution for ATP.

12. A method as defined in claim 11, wherein the insoluble chelating agent includes an iminodiacetic acid group.

13. A method as defined in claim 11, wherein the insoluble chelating agent is used in combination with a soluble agent, a diluent, a neutralizer of enzyme inhibitors, a soluble chelating agent, a cyclodextrin, a branched dextrin, a base, an alkaline phosphate buffer, or a mixture thereof.

14. A method as defined in claim 13, wherein the soluble chelating agent is selected from ethylenediamine, ethylenediaminetetraacetic acid (EDTA), ethylene glycol tetraacetic acid (EGTA), porphyrins, and mixtures thereof.

15. A method as defined in claim 11, wherein the insoluble chelating agent is in a form selected from powder, pelletized powder, bead, membrane, mesh, and mixtures thereof.

16. A method as defined in claim 13, wherein the alkaline phosphate buffer comprises a tribasic monovalent phosphate salt selected from trisodium phosphate, tripotassium phosphate, trilithium phosphate and mixtures thereof.

17. A method as defined in claim 11, wherein the cationic surfactant is selected from a quaternary ammonium salt, a phosphonium salt, benzalkonium chloride and tributyl (tetradecyl) phosphonium chloride.

* * * * *